(12) United States Patent
Caruso et al.

(10) Patent No.: US 8,470,984 B2
(45) Date of Patent: Jun. 25, 2013

(54) PROCESS FOR THE PREPARATION OF MORPHOLINYL ANTHRACYCLINE DERIVATIVES

(75) Inventors: Michele Caruso, Milan (IT); Vittoria Lupi, Milan (IT); Matteo Salsa, Novarese (IT)

(73) Assignee: Nerviano Medical Sciences S.R.L. (IT)

( * ) Notice: Subject to any disclaimer, the term of this patent is extended or adjusted under 35 U.S.C. 154(b) by 101 days.

(21) Appl. No.: 13/308,799

(22) Filed: Dec. 1, 2011

(65) Prior Publication Data
US 2012/0142906 A1   Jun. 7, 2012

Related U.S. Application Data

(60) Provisional application No. 61/418,949, filed on Dec. 2, 2010.

(51) Int. Cl.
*C07H 15/24* (2006.01)

(52) U.S. Cl.
USPC .................. 536/6.4; 536/18.5; 536/18.6

(58) Field of Classification Search
None
See application file for complete search history.

(56) References Cited

U.S. PATENT DOCUMENTS

| | | | |
|---|---|---|---|
| 4,672,057 A | 6/1987 | Bargiotti et al. | |
| 4,826,964 A | 5/1989 | Acton et al. | |
| 5,122,368 A | 6/1992 | Greenfield et al. | |
| 5,304,687 A | 4/1994 | Bargiotti et al. | |
| 5,387,578 A | 2/1995 | Angelucci et al. | |
| 5,776,458 A | 7/1998 | Angelucci et al. | |
| 5,843,903 A | 12/1998 | Schally et al. | |
| 6,630,579 B2 | 10/2003 | Chari et al. | |
| 7,223,837 B2 | 5/2007 | De Groot et al. | |
| 2007/0060534 A1 | 3/2007 | Matteucci et al. | |
| 2008/0241128 A1 | 10/2008 | Jeffrey | |
| 2010/0034837 A1 | 2/2010 | Beria et al. | |
| 2011/0076287 A1 | 3/2011 | Cohen et al. | |

FOREIGN PATENT DOCUMENTS

| | | |
|---|---|---|
| EP | 0 294 294 A2 | 12/1988 |
| GB | 2 247 885 A | 3/1992 |
| GB | 2 296 495 A | 7/1996 |
| WO | 98/02446 | 1/1998 |
| WO | WO 98/02446 A1 * | 1/1998 |
| WO | 2004/082579 A2 | 9/2004 |
| WO | 2004/082689 A1 | 9/2004 |
| WO | 2009/099741 A1 | 8/2009 |

OTHER PUBLICATIONS

Quintieri et al. Biochemical Pharmacology (2008), vol. 76, pp. 784-795.*
Acton et al., "New cyanormorpholinyl byproduct of doxorubicin reductive alkylation" J Med Chem. 29:1225-30 ( 1986).
Beulz-Riche et al., "Metabolism of methoxymopholino-doxorubicin in rat, dog and monkey liver microsomes: comparison with human microsomes" Fundam Clin Pharmacol 15:373-8 ( 2001).
King et al., "BR96 Conjugates of Highly Potent Anthracyclines" Bioorganic Medicinal Chemistry Letters Pergamon Elsevier Science 13(13):2119-2122 ( 2003).
King et al., "Monoclonal antibody conjugates of doxorubicin prepared with branched peptide linkers: Inhibition of aggregation by methoxytriethyleneglycol chains" Journal of Medical Chemistry 45:4336-4343 ( 2002).
Kratz et al., "Prodrugs of anthracyclines in cancer chemotherapy" Curr Med Chem 13:477-523 ( 2006).
Nagy et al., "Stability of cytotokic luteinizing hormone-releasing hormone conjugate (AN-152) containing doxorubicin 14-O-hemigutarate in mouse and human serum in vitro: implications for the design of preclinical studies" P Natl Acad Sci USA 97(2):829-34 (Jan. 18, 2000).
Quintieri et al., "Formation and antitumor activity of PNU-159682, a major metabolite of nemorubicin in human live microsomes" Clin Cancer Res 11:1608-17 (Feb. 15, 2005).
Quintieri et al., "In vitro hepatic conversion of the anticancer agent nemorubicin to its active metabolite PNU-159682 in mice, rats and dogs: a comparison with human liver microsomes" Biochem Pharmacol. 76:784-95 ( 2008).
Sessa et al., "Ongoing phase I and II studies of novel anthracyclines" Cardiovasc Toxicol 7:75-9 ( 2007).
Torgov et al., "Generation of an intensely potent anthracycline by a monoclonal antibody—B-galactosidase conjugate" Bioconjugate Chem 16:717-21 ( 2005).

* cited by examiner

*Primary Examiner* — Patrick Lewis
(74) *Attorney, Agent, or Firm* — Alex Andrus; Genentech, Inc.

(57) ABSTRACT

The present invention provides a process for the preparation of a morpholinyl anthracycline derivative in good yields and purity, including 3'-deamino-3"-4'-anhydro-[2"(S)-methoxy-3"(R)-hydroxy-4"-morpholinyl]doxorubicin (1).

7 Claims, No Drawings

PROCESS FOR THE PREPARATION OF MORPHOLINYL ANTHRACYCLINE DERIVATIVES

This non-provisional application filed under 37 CFR §1.53 (b), claims the benefit under 35 USC §119(e) of U.S. Provisional Application Ser. No. 61/418,949 filed on 2 Dec. 2010, which is incorporated by reference in entirety The invention relates to a process for the preparation of morpholinyl anthracycline derivatives characterized in that the morpholino ring is bridged with an oxygen atom to the position C-4' of the sugar residue.

These morpholinyl anthracycline derivatives, process for their preparation, pharmaceutical compositions comprising them and their use as therapeutic agents, particularly in the treatment of cancer, are described and claimed in International patent application WO 98/02446.

The morpholinyl anthracyclines are semisynthetic analogs of the anthracyclines and are endowed with remarkable anti-tumor activity (see: Bioactive Molecules Vol. 6, ED. J. W. Lown, Elsevier 1988; Curr Pharm Des. Mar. 5(3):217-27, 1999).

These compounds can be prepared according to known chemical processes by reacting the N-oxide derivative of a morpholinyl anthracycline derivative with an iron salt in presence of an iron-complexing agent as described in International patent application WO 98/02446 cited above.

Antibody conjugates of morpholinyl anthracyclines have targeted antitumor activity (WO 2009/099741; WO 2010/009124)

We have now surprisingly found that said morpholinyl anthracycline derivatives can be advantageously prepared through a novel process which allows the desired products to be obtained in high yields and purity.

Therefore, it is a first object of the present invention a process for preparing a morpholinyl anthracycline derivative of formula (I):

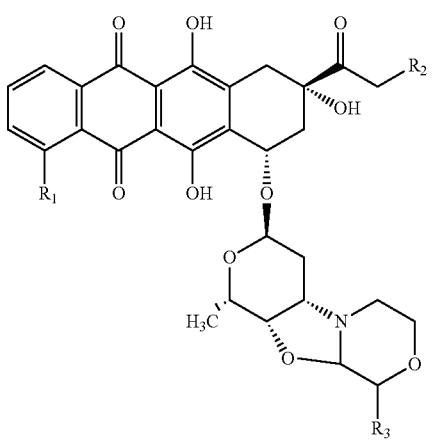

(I)

wherein
$R_1$ is hydrogen, OH or $OCH_3$,
$R_2$ is hydrogen, or OH and
$R_3$ is hydrogen or $OC_1$-$C_5$ alkyl, or a pharmaceutically acceptable acid addition salt thereof, which process comprises:
(i) reacting cyanuric chloride with an N-oxide anthracycline derivative of formula (II):

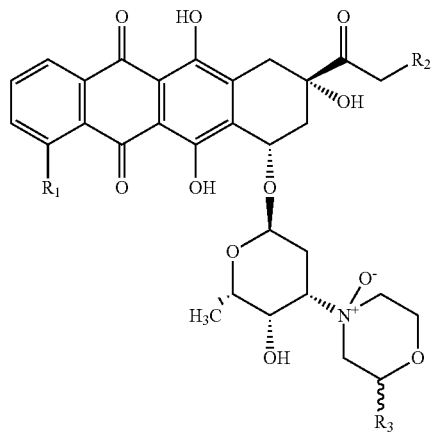

(II)

wherein $R_1$, $R_2$ and $R_3$ are as defined above, and
(ii) optionally, converting the resultant compound of formula (I) into a pharmaceutically acceptable acid addition salt thereof.

Exemplary specific morpholinyl anthracycline derivatives of formula (I) are the compounds listed below:
3'-deamino-3"-4'-anhydro-[2"(S)-methoxy-3"(R)-hydroxy-4"-morpholinyl]doxorubicin (1);
3'-deamino-3"-4'-anhydro-[2"(S)-methoxy-3"(R)-hydroxy-4"-morpholinyl]idarubicin (2);
3'-deamino-3"-4'-anhydro-[2"(S)-methoxy-3"(R)-hydroxy-4"-morpholinyl]daunorubicin (3);
3'-deamino-3"-4'-anhydro-[2"(S)-methoxy-3"(R)-hydroxy-4"-morpholinyl]caminomycin (4); and
3'-deamino-3"-4'-anhydro-[2"(S)-ethoxy-3"(R)-hydroxy-4"-morpholinyl]doxorubicin (5),
or a pharmaceutically acceptable acid addition salt thereof.

An exemplary specific morpholinyl anthracycline derivative of formula (I) is 3'-deamino-3"-4'-anhydro-[2"(S)-methoxy-3"(R)-hydroxy-4"-morpholinyl]doxorubicin (1). Formula (I) is a metabolite of nemorubicin, and is also known as PNU-159682, (Quintieri et al (2005) Clinical Cancer Research, 11(4):1608-1617; Beulz-Riche et al (2001) Fundamental & Clinical Pharmacology, 15(6):373-378; EP 0889898; WO 2004/082689; WO 2004/082579). PNU-159682 formula (1) is more cytotoxic than nemorubicin and doxorubicin in vitro, and is effective in in vivo tumor models. Antibody-drug conjugates comprising PNU-159682 formula (1) provide targeted cell-killing (WO 2010/009124).

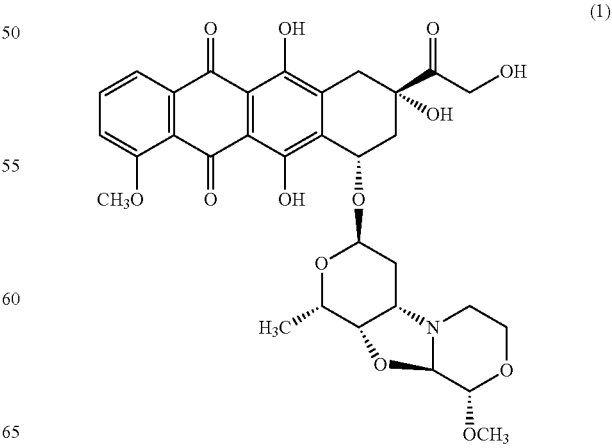

(1)

The term "OC$_1$-C$_5$ alkyl" refers to straight or branched saturated aliphatic hydrocarbyl groups having from 1 to 5 atoms and linked to the rest of the molecule through the oxygen atom.

The cyclization reaction of Example 1 proceeds with formation of single isomer. The reaction is typically performed in aprotic solvents such as dichloromethane, chloroform, acetone, 1,4-dioxane, dimethylformamide, 1,2-dichloroethane or acetonitrile and in presence of a base, such as triethylamine, 4-dimethylaminopyridine, sodium carbonate, cesium carbonate or potassium carbonate. The reaction is generally carried out from 0° C. to room temperature and from 5 to 60 minutes. Exemplary conditions are acetonitrile as solvent and potassium carbonate as base, at room temperature for 30 minutes.

The N-oxide starting compound of formula (II) can be prepared via dimethyldioxirane oxidation of a morpholinyl anthracycline derivative as described in GB 2 296 495 A.

The following morpholinyl anthracycline derivatives, generically described and claimed in International patent application WO 98/02446, as well as the pharmaceutical compositions comprising them and their use as therapeutic agents, particularly in the treatment of cancer, are new:

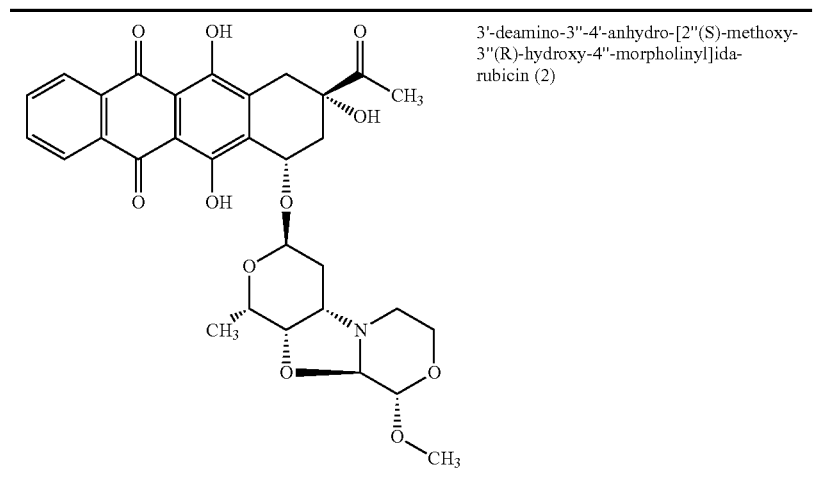

3'-deamino-3"-4'-anhydro-[2"(S)-methoxy-3"(R)-hydroxy-4"-morpholinyl]idarubicin (2)

(2)

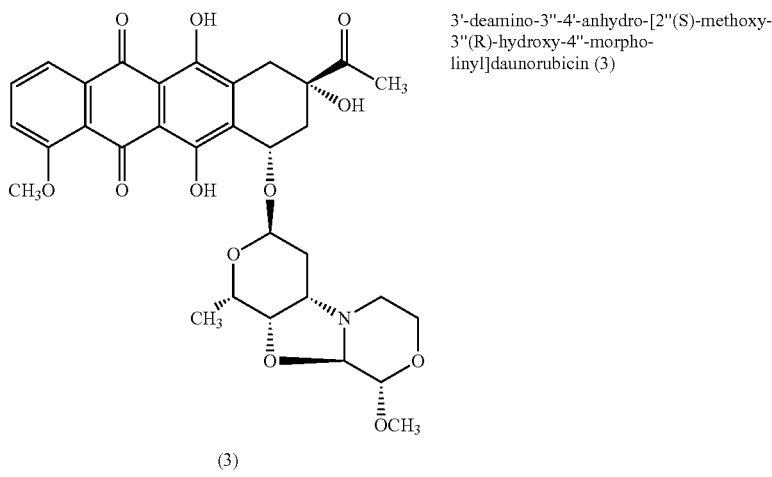

3'-deamino-3"-4'-anhydro-[2"(S)-methoxy-3"(R)-hydroxy-4"-morpholinyl]daunorubicin (3)

(3)

-continued

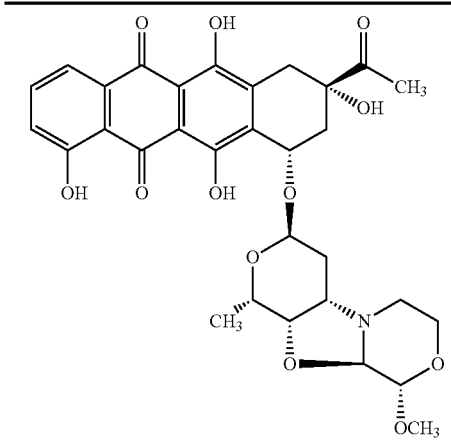

3'-deamino-3"-4'-anhydro-[2"(S)-methoxy-3"(R)-hydroxy-4"-morpholinyl]carminomycin (4)

(4)

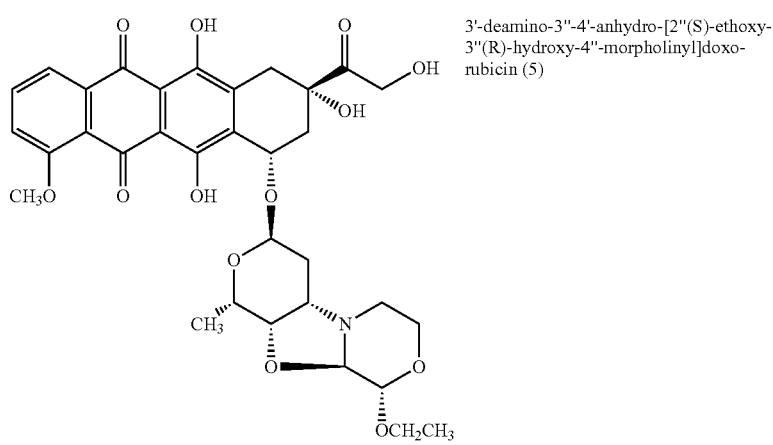

3'-deamino-3"-4'-anhydro-[2"(S)-ethoxy-3"(R)-hydroxy-4"-morpholinyl]doxorubicin (5)

(5)

Suitable routes of administration include parenteral administration. For parenteral administration a liquid formulation may be prepared using the active compound and a sterile diluent or carrier which may be either dissolve the active compound or provide a suspension of it. The parenteral formulation may be prepared in a form of a sterile solid for reconstitution prior to administration with a suitable vehicle such as physiological saline, sterile water or other sterile vehicle.

The compounds of the invention are useful in methods of treatment of hyperproliferative diseases such as leukemia, colon adenocarcinoma, and other solid tumors and hematological malignancies.

A therapeutically effective amount is administered to a patient having a hyperproliferative disease, such as a tumor, to ameliorate or improve the condition of the patient. An amount sufficient to inhibit progression of the disease, e.g. the growth of the tumor, may be administered. The dosage to be given can be ascertained using known dosage ranges for doxorubicin and daunorubicin modified by reference to the activity shown by the present compounds in vitro and in vivo anti-tumor test. Suitable dosage is generally in the range of from 0.01 to 100 mg/m$^2$, depending on the nature and severity of the disease being treated and on the general condition of the patient.

Biological Activity: In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% CO2 and after 72 hours the plates were processed using CellTiter-Glo® assay (Promega) following the manufacturer's instruction.

CellTiter-Glo® is a homogenous method based on the quantification of the ATP present, an indicator of metabolitically active cells. ATP is quantified using a system based on luciferase and D-luciferin resulting into light generation. The luminescent signal is proportional to the number of cells present in culture.

An amount of 25 microL/well of reagent solution is added to each well and after 5 minutes shaking, microplates are red by a luminometer to establish the IC50 values. The luminescent signal is proportional to the number of cells present in culture.

TABLE 1

In vitro cytotoxic activity ($IC_{50}$) of compounds of formula (I)

(I)

| compound | $R_1$ | $R_2$ | $R_3$ | A2780 ($IC_{50}$ picoM) | MCF7 ($IC_{50}$ picoM) |
|---|---|---|---|---|---|
| 1 | OMe | OH | OMe | 0.024 | 0.022 |
| 2 | H | H | OMe | 0.000807 | 0.000912 |
| 3 | OMe | H | OMe | 0.000817 | 0.00144 |
| 4 | OH | H | OMe | 0.000421 | 0.000721 |
| 5 | OMe | OH | OEt | 0.000321 | 0.00714 |

The following examples illustrate but do not limit the scope of the invention.

EXAMPLE 1

3'-deamino-3"-4'-anhydro-[2"(S)-methoxy-3"(R)-hydroxy-4"-morpholinyl]doxorubicin (1)

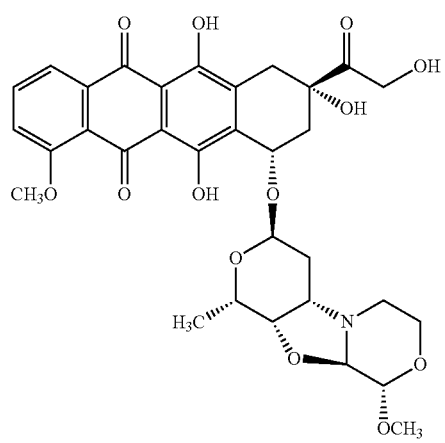

To a solution 3'-deamino-3'[2(S)-methoxy-4-morpholinyl]-doxorubicin N-oxide (prepared as described in GB 296495 A) (50.0 mg, 0.076 mmol) in 12.5 ml of dry acetonitrile, powdered potassium carbonate (31.5 mg, 0.228 mmol) and cyanuric chloride (2,4,6-Trichloro-1,3,5-triazine, CAS Reg. No. 108-77-0, 28.0 mg, 0.152 mmol) were added. The reaction mixture was vigorously stirred in the dark at room temperature for 20 minutes, until no starting material was detectable (TLC analysis, $EtOH:CH_2Cl_2=1:9$). A solution of 3-amino-1,2-propanediol (42.0 mg, 0.46 mmol) in water (1 ml) was then added to the reaction mixture and the aqueous phase was extracted with dichloromethane (4×30 ml). The combined organic phases were dried over anhydrous sodium sulphate, filtered and evaporated under vacuum. The crude was purified by flash column chromatography ($EtOH:CH_2Cl_2=0.2:9.8$) on silica gel (230-400 mesh), affording 24.4 mg of 3'-deamino-3"-4'-anhydro-[2"(S)-methoxy-3"(R)-hydroxy-4"-morpholinyl]doxorubicin (1) as a red solid (yield=50%). $^1$H NMR (500 MHz, ACETONITRILE-$d_3$) δ ppm 1.29 (d, J=6.41 Hz, 3H) 1.68 (dt, J=15.02, 5.86 Hz, 1H) 1.89 (dt, J=15.02, 5.50 Hz, 1H) 2.07-2.13 (m, 1H) 2.46 (dt, J=14.66, 2.02 Hz, 1H) 2.69-2.75 (m, 1H) 2.76-2.81 (m, 1H) 2.95 (d, J=18.50 Hz, 1H) 3.08 (t, J=5.50 Hz, 1H) 3.14 (dd, J=18.59, 1.92 Hz, 1H) 3.37 (s, 3H) 3.41-3.47 (m, 1H) 3.52-3.58 (m, 1H) 3.73 (ddd, J=11.50, 8.11, 2.93 Hz, 1H) 4.01 (s, 3H) 4.02-4.08 (m, 2H) 4.25 (d, J=2.93 Hz, 1H) 4.53 (d, J=2.93 Hz, 1H) 4.61 (s, 1H) 4.63-4.75 (m, 2H) 5.22 (dd, J=3.94, 2.11 Hz, 1H) 5.36 (t, J=5.59 Hz, 1H) 7.54 (d, J=8.06 Hz, 1H) 7.84 (t, J=8.06 Hz, 1H) 7.96 (dd, J=7.69, 0.73 Hz, 1H). MS (ESI): 642 [M+H]+. Retention time=4.88

According to the same methodology used for the preparation of 3'-deamino-3"-4'-anhydro-[2"(S)-methoxy-3"(R)-hydroxy-4"-morpholinyl]doxorubicin (1), but employing suitable substituted derivatives, the following compounds were prepared:

3'-deamino-3"-4'-anhydro-[2"(S)-methoxy-3"(R)-hydroxy-4"-morpholinyl]idarubicin (2)

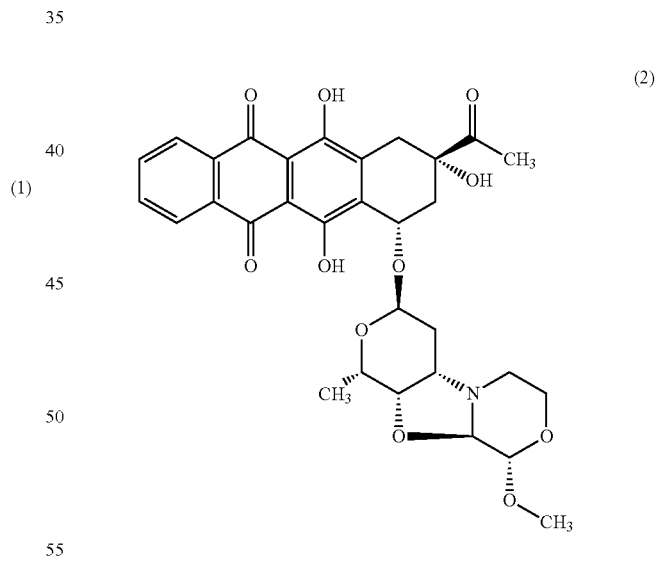

$^1$H NMR (ACETONITRILE-$d_3$) δ: 8.29-8.34 (m, 2H), 7.86-7.95 (m, 2H), 5.35 (t, J=5.6 Hz, 1H), 5.19 (dd, J=4.1, 2.1 Hz, 1H), 4.54 (s, 1H), 4.54 (s, 1H), 4.26 (d, J=2.9 Hz, 1H), 4.09 (dd, J=6.6, 1.7 Hz, 1H), 4.03 (dd, J=7.1, 1.8 Hz, 1H), 3.74 (ddd, J=11.5, 8.2, 3.0 Hz, 1H), 3.51-3.58 (m, 1H), 3.44 (q, J=6.0 Hz, 1H), 3.37 (s, 3H), 3.06-3.11 (m, 1H), 2.91-2.98 (m, 1H), 2.67-2.81 (m, 2H), 2.44 (dt, J=14.8, 2.1 Hz, 1H), 2.35 (s, 3H), 2.06 (dd, J=14.6, 4.4 Hz, 1H), 1.85-1.91 (m, 1H), 1.71 (dt, J=15.0, 5.9 Hz, 1H), 1.29 (d, J=6.6 Hz, 3H). MS calc: 596.2127; MS found: 596.2117. MS (ESI): 596 [M+H]+. Retention time=6.32 min

3'-deamino-3"-4'-anhydro-[2"(S)-methoxy-3"(R)-hydroxy-4"-morpholinyl]daunorubicin (3)

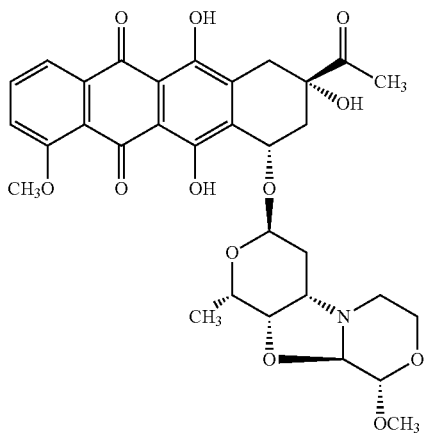

(3)

$^1$H NMR (ACETONITRILE-d$_3$) δ: 7.94-7.99 (m, 1H), 7.84 (t, J=8.1 Hz, 1H), 7.54 (d, J=8.5 Hz, 1H), 5.35 (t, J=5.5 Hz, 1H), 5.19 (m, 1H), 4.55 (s, 1H), 4.54 (d, J=2.9 Hz, 1H), 4.26 (d, J=2.7 Hz, 1H), 4.09 (dd, J=6.6, 1.7 Hz, 1H), 3.97-4.05 (m, 4H), 3.74 (, 1H), 3.54 (m, 1H), 3.44 (q, J=6.1 Hz, 1H), 3.37 (s, 3H), 3.02-3.10 (m, 1H), 2.88-3.01 (m, 1H), 2.64-2.86 (m, 2H), 2.43 (dt, J=14.8, 2.1 Hz, 1H), 2.34 (s, 3H), 2.05 (dd, J=14.7, 4.3 Hz, 1H), 1.88 (dt, J=15.1, 5.7 Hz, 1H), 1.70 (dt, J=15.1, 5.8 Hz, 1H), 1.29 (d, J=6.6 Hz, 3H) MS calc: 626.2232; MS found: 626.2208. MS (ESI): 626 [M+H]$^+$. Retention time=5.66 min

3'-deamino-3"-4'-anhydro-[2"(S)-methoxy-3"(R)-hydroxy-4"-morpholinyl]caminomycin (4)

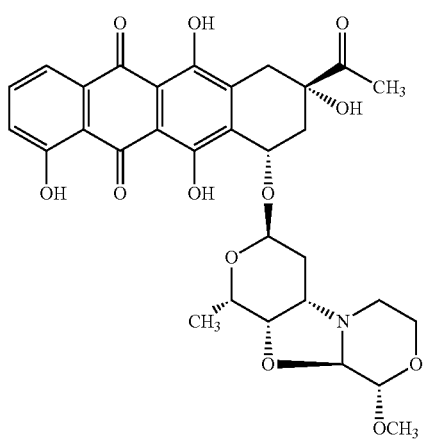

(4)

$^1$H NMR (ACETONITRILE-d$_3$) δ: 7.81-7.91 (m, 1H), 7.84 (m, 1H), 7.35 (dd, J=8.3, 1.1 Hz, 1H), 5.24-540 (m, 1H), 5.19 (m, 1H), 4.54 (d, J=2.9 Hz, 1H), 4.53 (s, 1H), 4.26 (d, J=2.9 Hz, 1H), 4.06-4.14 (m, 1H), 4.04 (dd, J=7.1, 1.8 Hz, 1H), 3.74 (m, 1H), 3.55 (m, 1H), 3.45 (m, 1H), 3.37 (s, 3H), 3.07-3.11 (m, 1H), 2.94-2.98 (m, 1H), 2.69-2.80 (m, 2H), 2.42-2.46 (m, 1H), 2.35 (s, 3H), 1.99-2.11 (m, 1H), 1.85-1.92 (m, 1H), 1.66-1.75 (m, 1H), 1.29 (d, J=6.56 Hz, 2H). MS calc: 612.2076; MS found: 612.2054. MS (ESI): 612 [M+H]$^+$. Retention time=6.28 min

3'-deamino-3"-4'-anhydro-[2"(S)-ethoxy-3"(R)-hydroxy-4"-morpholinyl]doxorubicin (5)

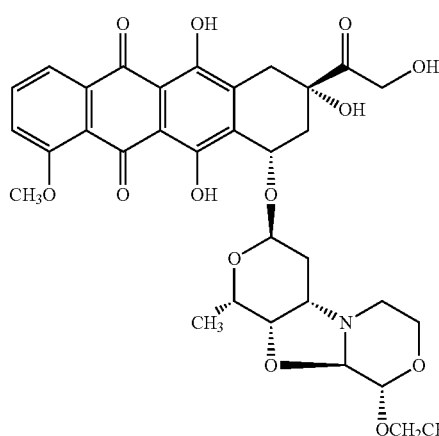

(5)

$^1$H NMR (ACETONITRILE-d$_3$) δ: 7.96 (d, J=7.6 Hz, 1H), 7.83 (t, J=8.1 Hz, 1H), 7.53 (d, J=8.4 Hz, 1H), 5.36 (t, J=5.6 Hz, 1H), 5.21 (br. s., 1H), 4.69 (t, J=5.4 Hz, 2H), 4.63 (d, J=2.4 Hz, 1H), 4.62 (s, 1H), 4.24 (s, 1H), 4.04-4.04 (m, 2H), 4.00 (s, 3H), 3.70-3.82 (m, 2H), 3.37-3.60 (m, 3H), 3.13 (d, J=18.8 Hz, 1H), 3.08 (t, J=5.3 Hz, 1H), 2.94 (d, J=18.6 Hz, 1H), 2.66-2.83 (m, 2H), 2.46 (d, J=14.9 Hz, 1H), 2.07-2.12 (m, 1H), 1.86-1.92 (m, 1H), 1.63-1.77 (m, 1H), 1.29 (d, J=6.4 Hz, 3H), 1.20 (t, J=7.1 Hz, 3H). MS calc: 656.2338; MS found: 656.2325 MS (ESI): 656 [M+H]$^+$. Retention time=5.22 min HPLC/MS Analytic Method The HPLC equipment consisted of a Waters 2795 Alliance HT® system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software. HPLC was carried out at 30° C. at a flow rate of 1.0 mL/min using a Waters X Terra MS C18-3.5 μM (4.6×50 mm) column. Mobile phase A was ammonium acetate 5 mM pH=5.2 buffer with acetonitrile (95:5), and mobile phase B was H$_2$O/acetonitrile (5:95); the gradient was from 10 to 90% B in 8 minutes then ramp to 100% B in 1.0 minutes. The mass spectrometer was operated in positive and in negative ion mode, the capillary voltage was set up at 3.5 kV (ES$^+$) and 28 V (ES$^-$); the source temperature was 120° C.; cone was 14 V (ES$^+$) and 2.8 kV (ES$^-$); full scan, mass range from 100 to 1000 m/z was set up.

The invention claimed is:

1. A process for preparing a morpholinyl anthracycline derivative of formula (I):

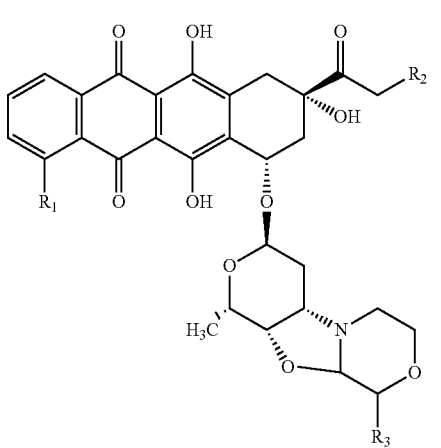

wherein
$R_1$ is hydrogen, OH or $OCH_3$;
$R_2$ is hydrogen, or OH; and
$R_3$ is hydrogen or $OC_1$-$C_5$ alkyl, or a pharmaceutically acceptable acid addition salt thereof;
which process comprises reacting cyanuric chloride and an N-oxide anthracycline derivative of formula (II):

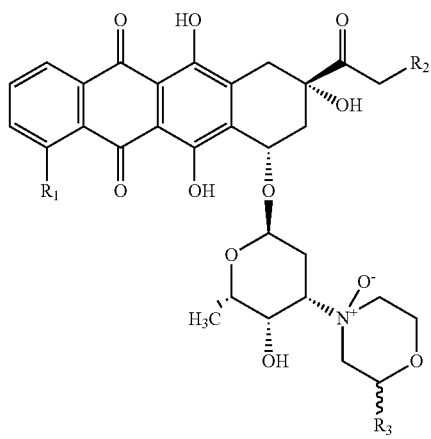

where $R_1$, $R_2$ and $R_3$ are as defined above; and
whereby the morpholinyl anthracycline derivative of formula (I) is formed.

2. The process according to claim 1 wherein the reaction of a compound of formula (II) to give a compound of the formula (I) is performed in an aprotic solvent selected from dichloromethane, chloroform, acetone, 1,4-dioxane, dimethylformamide, 1,2-dichloroethane and acetonitrile.

3. The process according to claim 1 characterized in that the compound of formula (I) is 3'-deamino-3"-4'-anhydro-[2"(S)-methoxy-3"(R)-hydroxy-4"-morpholinyl]doxorubicin.

4. The process according to claim 1 further comprising converting the resultant product formula (I) into a pharmaceutically acceptable acid addition salt thereof.

5. The process according to claim 1 wherein the reaction of a compound of formula (II) to give a compound of the formula (I) is performed in the presence of a base selected from triethylamine, 4-dimethylaminopyridine, sodium carbonate, cesium carbonate and potassium carbonate.

6. A compound selected from:
3'-deamino-3"-4'-anhydro-[2"(S)-methoxy-3"(R)-hydroxy-4"-morpholinyl]idarubicin (2);
3'-deamino-3"-4'-anhydro-[2"(S)-methoxy-3"(R)-hydroxy-4"-morpholinyl]daunorubicin (3);
3'-deamino-3"-4'-anhydro-[2"(S)-methoxy-3"(R)-hydroxy-4"-morpholinyl]caminomycin (4); and
3'-deamino-3"-4'-anhydro-[2"(S)-ethoxy-3"(R)-hydroxy-4"-morpholinyl]doxorubicin (5),
or a pharmaceutically acceptable acid addition salt thereof.

7. The compound of claim 6 prepared by a process comprising the step wherein cyanuric chloride is reacted with an N-oxide anthracycline derivative of formula (II):

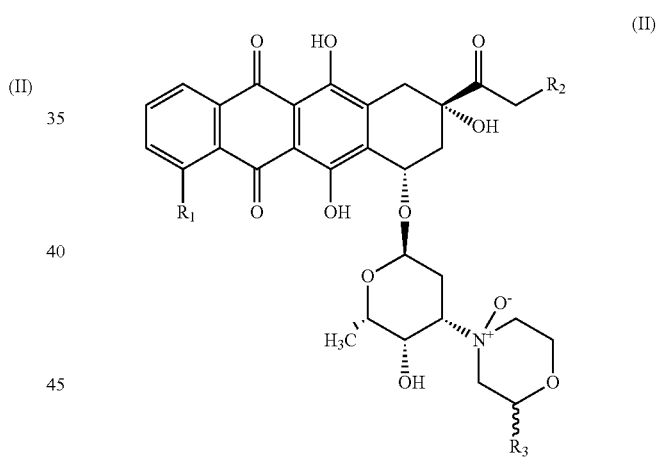

where
$R_1$ is hydrogen, OH or $OCH_3$;
$R_2$ is hydrogen, or OH; and
$R_3$ is hydrogen or $OC_1$-$C_5$ alkyl.

* * * * *